(12) United States Patent
Worth et al.

(10) Patent No.: US 9,702,817 B2
(45) Date of Patent: Jul. 11, 2017

(54) METHOD AND APPARATUS FOR TESTING OF ENGINE COMPONENTS

(71) Applicant: ROLLS-ROYCE plc, London (GB)

(72) Inventors: Nicholas A Worth, Norwich (GB); Stephen C. Harding, Bristol (GB)

(73) Assignee: ROLLS-ROYCE plc, London (GB)

( * ) Notice: Subject to any disclaimer, the term of this patent is extended or adjusted under 35 U.S.C. 154(b) by 61 days.

(21) Appl. No.: 14/978,498

(22) Filed: Dec. 22, 2015

(65) Prior Publication Data
US 2016/0195474 A1    Jul. 7, 2016

(30) Foreign Application Priority Data

Jan. 6, 2015 (GB) ..................................... 1500122

(51) Int. Cl.
*G01N 21/00* (2006.01)
*G01N 21/53* (2006.01)
(Continued)

(52) U.S. Cl.
CPC ............. *G01N 21/53* (2013.01); *F01D 5/186* (2013.01); *F01D 21/003* (2013.01);
(Continued)

(58) Field of Classification Search
CPC ............... G01N 21/53; G01N 15/0205; G01N 15/1459; G01N 21/51; G01N 15/1434
(Continued)

(56) References Cited

U.S. PATENT DOCUMENTS 6,387,331 B1 * 5/2002 Hunter ................ B01F 13/0071
356/244
6,524,395 B1    2/2003 Devine, II
(Continued)

FOREIGN PATENT DOCUMENTS

EP        2103928 A2    9/2009

OTHER PUBLICATIONS

May 17, 2016 Search Report issued in European Patent Application No. 15 20 1936.
(Continued)

*Primary Examiner* — Tarifur Chowdhury
*Assistant Examiner* — Md M Rahman
(74) *Attorney, Agent, or Firm* — Oliff PLC

(57) ABSTRACT

Method and apparatus testing engine component, for blockage of one or more through-holes in a portion of a wall. The method including (i) providing a supply of test fluid, (ii) causing or permitting flow of test fluid to occur from first to second region, (iii) illuminating the second region with electromagnetic radiation to cause scattering of electromagnetic radiation by material exiting substantially non-blocked through-holes in wall portion having passed therethrough from the first to second side, (iv) detecting said scattering of electromagnetic radiation from said substantially non-blocked through-holes; and (v) comparing said detected scattering of electromagnetic radiation from said substantially non-blocked holes with known pattern of through-holes in component wall portion to determine the presence and/or location and/or identity of any blocked or partially blocked through-holes in component wall portion.

15 Claims, 2 Drawing Sheets

(51) Int. Cl.
　　*G01M 15/14*　　(2006.01)
　　*G01N 21/64*　　(2006.01)
　　*F01D 21/00*　　(2006.01)
　　*G01N 21/956*　　(2006.01)
　　*F01D 5/18*　　(2006.01)

(52) U.S. Cl.
　　CPC ............ *G01M 15/14* (2013.01); *G01N 21/64* (2013.01); *G01N 21/95692* (2013.01); *B23P 2700/06* (2013.01); *F05D 2260/202* (2013.01); *F05D 2260/607* (2013.01); *F05D 2260/83* (2013.01); *G01N 2201/023* (2013.01)

(58) Field of Classification Search
　　USPC ........................................................ 356/338
　　See application file for complete search history.

(56) References Cited

U.S. PATENT DOCUMENTS

| | | | |
|---|---|---|---|
| 7,597,852 B2* | 10/2009 | Desrosiers | B01L 3/5085 |
| | | | 250/428 |
| 7,741,629 B2* | 6/2010 | Schwarz | G01N 21/474 |
| | | | 250/559.01 |
| 2004/0263837 A1 | 12/2004 | Kimberlin | |
| 2007/0022724 A1 | 2/2007 | Gargano et al. | |
| 2007/0238191 A1 | 10/2007 | Gargano et al. | |
| 2010/0201983 A1 | 8/2010 | Hatano et al. | |
| 2012/0297863 A1 | 11/2012 | Wood et al. | |

OTHER PUBLICATIONS

Jun. 22, 2015 Search Report issued in Great Britain Patent Application No. 1500122.5.

* cited by examiner (a) (b)

(a) (b)

METHOD AND APPARATUS FOR TESTING OF ENGINE COMPONENTS

TECHNICAL FIELD

This invention relates to the testing of engine components, especially components of gas turbine engines, and to a method and apparatus for so doing. More particularly, though not exclusively, the invention relates to the testing of engine components which comprise one or more holes, often a large number of holes, e.g. for cooling purposes, to determine if any of such holes are blocked.

BACKGROUND OF THE INVENTION AND PRIOR ART

Various components in gas turbine engines utilise arrangements of through-holes in their walls for the purpose of establishing various kinds and configurations of cooling arrangements therein. Such components may include for example combustor cassettes, combustion chamber heat shields and barrels, turbine blades, guide vanes, exhaust ducts and so on, and they are often manufactured by conventional investment casting techniques. Typically such components include small, substantially straight through-holes, often a plurality or even a large number thereof, which extend through the thickness of a wall of the component in order to extract heat from the material of the component body typically by producing a uniform film of a cooling fluid, e.g. cooling air, on the hot outer surface of the component. One method of extracting a larger amount of heat from the material than might otherwise be possible is to use two separate but closely spaced walls instead of one only thereof. In one simple constructional form, the hotter (inner) wall may be manufactured as a separate cast tile component which is bolted onto the cooler (outer) wall, thereby enabling a high temperature-capable cast alloy to be used for the inner wall.

The use of such small through-holes for film cooling can present difficulties in servicing, maintenance and/or repair procedures, as it is often necessary to be able to detect whether any—or any appreciable number—of the holes are blocked, e.g. as a result of the presence or build-up of combustion or other deposits such as dirt, pollution or environmental residues during extended use of the engine, or even as a result of remnant material left over from the manufacture of the component itself. Hole blockages can pose significant mechanical and safety risks, since a hole that is blocked cannot pass therethrough a required flow of cooling fluid, which may result—especially if several or many holes are blocked simultaneously—in the component overheating, or even ultimately prematurely failing. There is therefore a general need in the art to be able to routinely and efficiently inspect or test components for determining whether—and/or to what extent—any such through-holes are blocked.

In the above-mentioned simple dual-walled cooling arrangement, since the two walls are separate components and because they use straight holes, the task of inspecting the holes for blockages can be relatively straightforward. For example, the two wall components may be detached from one another, and a simple visual inspection procedure used, in which each component in turn is placed in front of a strong visible light source, and the line-of-sight direction through each hole is used to visually inspect it for possible blockage: if a hole is clear (i.e. not blocked), then light gets through to the observer and that can be readily seen and noted, whereas if a hole is blocked (or partially blocked), then no (or only limited) light gets through to the observer. Again, that can be readily seen by the observer's eye and noted, thereby enabling appropriate action to be taken to unblock the identified hole.

The above relatively simple known procedure is illustrated schematically in FIG. 1 of the accompanying drawings. In FIG. 1(a) the two wall components 2 (inner), 4 (outer) are shown mounted in juxtaposition, as they are in use, with their respective cooling through-holes labelled as 12, 14. In FIG. 1(b) the two wall components 2, 4 have been separated, thereby enabling each component in turn to be inspected by illuminating each one with a strong visible light source 20. The line-of-sight direction (indicated by the dotted line) through each hole 12, 14 allows the observer 30 to observe each hole 12, 14 to determine whether—and/or to what relative extent—light is passing through it. This therefore constitutes a direct visual indicator of whether the respective hole 12, 14 is clear or whether it is blocked, or perhaps partially blocked, and as a result of that determination appropriate remedial action to unblock the identified hole can be taken.

In some more modern gas turbine engines, certain through hole-cooled components such as those mentioned above are increasingly being manufactured using additive layer manufacturing (ALM) methods, which involve building up the component walls and other features incrementally from a laser-fusible powder of the required component material. Such ALM methods can be particularly useful because they allow the creation of relatively complex designs of components in a relatively simple and cheap manner. This can for example include mechanically integrated designs of cooling arrangements comprising virtually any number and arrangement of through-holes in individual skins or walls of multi-walled or integral box-like components, which using ALM techniques may thus be formed essentially as unitary bodies. This may lead for instance to significant weight and cost advantages, because of the ability to reduce wall thicknesses compared with what is possible using conventional casting techniques, whilst maintaining structural integrity and strength of the component. Examples of such components include those comprising mechanically integrated impingement effusion cooling systems.

However, the use of ALM methods comes with new disadvantages with respect to being able to inspect such components for potential blockage of through-holes in the walls thereof using a conventional line-of-sight inspection technique using visible light as discussed above. This is because although ALM manufacturing tolerances allow accurate relative positioning between e.g. impingement and effusion holes, this is only possible by building both hot and cold walls of a multi-walled component as a single integrated piece, and in that case through-holes in each respective wall may often not be in alignment such as to permit use of the above line-of-sight inspection technique. Furthermore ALM methods also allow complex, non-straight through-hole shapes to be manufactured, which can be useful to employ in practice but which again may prevent the use of the above line-of-sight inspection technique because of the absence of a direct straight line light path through such a non-straight hole configuration. Moreover, in the case of unitary multi-walled components which define a void between a pair of walls, e.g. spaced apart "hot" and "cold" walls formed in a single piece with each wall containing its own arrangement of through-holes (perhaps even straight holes), the mere presence of the void may also often prevent use of the above line-of-sight inspection technique, since through-holes of the respective sets in the facing walls may often be arranged with their longitudinal axes non-coincident, in which case it is impossible for light to pass through both sets of holes simultaneously even if both holes of a given pair in the two walls are clear/unblocked.

Examples of the preceding arrangements are illustrated schematically in FIG. 2 of the accompanying drawings. In FIG. 2(a) the two wall components 2' (inner), 4' (outer) are shown as a unitarily formed integrated piece, with their respective cooling through-holes labelled as 12', 14'. As often may be the case in practice, the respective pairs of through-holes 12', 14' are not in register, i.e. their respective longitudinal axes are not coincident, so light from the light source 20 is prevented from reaching an observer 30 even if the holes 12', 14' are clear/unblocked. On the other hand, FIG. 2(b) shows a complex hole arrangement in which a non-straight complex hole 12" in the wall component 2" cannot even itself transmit a straight beam of light from the light source 20 to the observer 30, owing to the non-straight configuration of the hole passage itself.

Thus, in many modern manufacturing techniques for engine components comprising various arrangements and configurations of one or more through-holes in at least one wall thereof, conventional line-of sight inspection techniques are impossible to use.

Hitherto in the published art there have been several proposals for inspection systems for testing engine components for partial or complete blockage of through-holes in walls thereof. These have included for example systems based on measuring flow rates of a test liquid pumped through selected through-holes in the component, or mapping infra-red signatures or hotspots produced by impinging jets of steam passing through the holes, or even positron emission tomography. Such known systems are generally complex, expensive and slow to implement on a large industrial scale, and they also fail to address at least some of the specific problems associated with modern component manufacturing methods, such as ALM, as discussed above.

It is therefore a primary object of the present invention to address the above shortcomings of the prior art.

SUMMARY OF THE INVENTION

Accordingly, aspects of the present invention relate to a method and an apparatus.

In a first aspect the present invention provides a method for testing an engine component for blockage of one or more through-holes in at least a portion of a wall thereof, wherein the portion of the wall comprises a known pattern of through-holes therein extending between first and second sides of the wall, the method comprising:
  (i) providing in a first region to the first side of the wall a supply of a test fluid, wherein the test fluid comprises a material able to scatter electromagnetic radiation incident thereon;
  (ii) causing or permitting a flow of the test fluid to occur from the first region to a second region to the second side of the wall;
  (iii) illuminating the second region with electromagnetic radiation to cause scattering of electromagnetic radiation by material exiting substantially non-blocked through-holes in the wall portion having passed therethrough from the first side to the second side;
  (iv) detecting said scattering of electromagnetic radiation from said substantially non-blocked through-holes; and
  (v) comparing said detected scattering of electromagnetic radiation from said substantially non-blocked holes with the known pattern of through-holes in the component wall portion to determine the presence and/or location and/or identity of any blocked or partially blocked through-holes in the component wall portion.

In a second aspect the present invention provides apparatus for testing an engine component for blockage of one or more through-holes in at least a portion of a wall thereof, wherein the portion of the wall comprises a known pattern of through-holes therein extending between first and second sides of the wall, the apparatus comprising:
  a supply of a test fluid located in a first region to the first side of the wall, wherein the test fluid comprises a material able to scatter electromagnetic radiation incident thereon,
  an illumination device located in a second region to the second side of the wall for illuminating said second region with electromagnetic radiation to cause scattering of electromagnetic radiation by material exiting substantially non-blocked through-holes in the wall portion having passed therethrough from the first side to the second side of the wall under a flow of the test fluid caused or permitted to occur from the first side to the second side,
  a detector device for detecting said scattering of electromagnetic radiation from said substantially non-blocked through-holes, and
  a comparator device for comparing said detected scattering of electromagnetic radiation from said substantially non-blocked holes with the known pattern of through-holes in the component wall portion to determine the presence and/or location and/or identity of any blocked or partially blocked through-holes in the component wall portion.

Embodiments of the present invention exploit the phenomenon of scattering of electromagnetic radiation by an "active" material which is able to scatter electromagnetic radiation, in order to provide a comparative map of scattered and non-scattered radiation in or entering the second region to the second side of the component wall, or portion thereof, being tested. By detecting any scattered radiation in that second region, the presence, location and/or intensity of which is indicative of material having passed through one or more substantially unblocked through-holes in the wall portion from the first to the second side, and then comparing that detected scattering pattern with the general known pattern of through-holes in the portion of the wall under test, it is possible to readily determine the existence and/or location and/or identity of any through-holes in the wall portion which are blocked or partially blocked.

Although it might be expected that the principle of radiation scattering from a large number of scattering surfaces would mean that generally a detected scattering signal may not be proportional to an effective cross-sectional flow area in the through-hole(s) under test (and thus not a quantitative measure of the degree of blockage thereof), embodiments of the invention circumvent this by using a technique which does not depend on such proportionality to produce a meaningful and useful result.

In preferred embodiments of the invention the electromagnetic radiation may be of any suitable wavelength or frequency, which may for example depend on the active material which is to be used to scatter that radiation when incident thereon. In many practical embodiments electromagnetic radiation in the visible portion of the spectrum may conveniently be used. Such visible light may not only be useful with respect to enabling the active scattering material to be selected from a wider variety of such materials, but it may also enable readily available and cheap detecting devices to be utilised. However, it is to be understood that other wavelengths or frequencies of electromagnetic radiation may alternatively be used, e.g. infra-red or ultra-violet radiation, or even radiation of other wavelengths/frequencies, provided of course that the active scattering material and the type of detector device are selected accordingly.

In embodiments of the invention the active scattering material may be selected from a wide variety of such materials, with the general proviso that it should be able to scatter the light or other electromagnetic radiation incident thereon to an extent that permits such scattering to be readily detected and quantified by the detector device. In general it may be preferred that the active material acts to scatter incident light or other radiation to as large a degree and/or extent and/or angle and/or intensity as possible, in order to facilitate the task of detecting the thus scattered light or other radiation. Such scattering may occur through various mechanisms of interaction between the incident light or other electromagnetic radiation and the active material, such as any one or more of reflection, diffraction, refraction or other form of scattering.

In various embodiments, and preferably depending at least partly on the identity of the active scattering material used, the active scattering material may be provided in the form of particles of a solid material or as particles or droplets of a liquid material. Either form of particles may in some embodiments be provided as dispersed (or possibly even dissolved) particles or micro-particles in a carrier medium, especially a fluid carrier medium, whereby the above-defined test fluid may in some embodiments comprise the said carrier medium with the said particles of active material dispersed (or possibly even dissolved) therein. The carrier medium may be a liquid or, more preferably, a gas, e.g. air. A gaseous carrier medium may in some embodiments be particularly preferred, as it may be more easily provided as a supply thereof and may be easier to be caused or permitted to flow from the first region to the second region by natural convection or pumping.

Thus, is some embodiments of the invention the test fluid may conveniently comprise a colloidal dispersion, suspension or solution of the active scattering material, in the form of solid or liquid particles, in a fluid, especially a gaseous, carrier medium. Accordingly, in some embodiments of the invention, where the active scattering material is in the form of particles (solid or liquid), the particles may typically for example have an average particle size in the range of from about 1 nm to about 1 µm. Optionally, particle sizes of the active material in excess of 1 µm, e.g. up to about 5 or 10 or 20 or 50 or even 100 µm, or possibly even greater, may in certain cases be used, if the carrier medium and active material are selected accordingly so that the test fluid is a stable composition and its components remain in their respective physical states without settling, precipitation or separation during the testing method. Generally it is preferred to use particle sizes of the active material which are significantly smaller than the minimum diameter of the through-holes of the component wall, or portion thereof, under test, in order to minimise or eliminate any risk of the test fluid itself blocking the holes during the test procedure.

Suitable active scattering materials for use in embodiments of the invention may include for example solid micro-particles of titanium dioxide ($TiO_2$), flakes of aluminium (Al) metal, or a suitable smoke material. Gaseous dispersions of various radiation-scattering oils may also be used as the active scattering material. Examples of suitable light-scattering oils may include olive oil, vegetable oils, odena oil. Another example of a suitable light-scattering material is water, especially in the form of water droplets or vapour, e.g. in the form of dry-ice-condensed water vapour. Yet another example of a suitable light-scattering material is micro-particles or micro-spheres of glass or a glass material, which materials may often suitably be employed in the form of a dispersion thereof in a liquid carrier medium. Optionally, particles of one or more coloured light-scattering materials and/or fluorescent materials may be used as the, or as a component of the, active scattering material, in order to provide enhanced optical contrast in the detection of light-scattering flows and/or to assist in discriminating between detected scattered signals and the relevant background.

Any such active scattering materials may be used either singly or in any combination of two or more such materials.

The active scattering material may be present in the test fluid, e.g. in the carrier gas or other fluid in preferred embodiments, in any suitable or desired concentration, with the general proviso that it should be present in such an amount that it scatters the light or other electromagnetic radiation incident thereon to an extent that permits such scattering to be readily detected and quantified by the detector device.

In practical embodiments of the invention the supply of the fluid may be in the form of a reservoir of the test fluid, e.g. a container thereof. The container or reservoir may itself be provided in or at the first region to the first side of the component wall to be tested. Alternatively the container or reservoir may be provided remote from the first region yet linked thereto by a supply conduit, pipe, or other supply route to provide the necessary supply of the test fluid in or at the said first region.

In some forms of implementation of the invention the supply of test fluid may be provided by a portion of the apparatus comprising an enclosure or plenum which defines a chamber within which a volume of the test fluid may be stored or provided for supply to the component being tested. The chamber may conveniently be configured for placement in the said first region to the said first side of the component wall to be tested.

In some practical embodiments, the chamber may be configured to be placeable against a sidewall of the component whose wall portion with through-holes therein is to be tested. In some instances that sidewall against which the chamber is placeable may be the said component wall portion with through-holes which is to be tested. However, in other instances that sidewall against which the chamber is placeable may be an additional wall of the component, preferably an additional wall with one or more through-holes therein, which is spaced from and/or joined to the said wall portion to be tested. In such latter cases where such an additional wall is that against which the chamber is placeable, because that additional wall preferably still needs to allow test fluid to flow from the supply thereof in the first region to the wall portion being tested, that additional wall preferably still contains one or more through-holes therein for allowing test fluid to flow therethrough to reach the first side of the component wall portion under test. However, since in this case that additional wall is not the component wall being tested, it may not matter or be critical how many such through-holes is/are provided in that additional wall, or possibly even whether they are all clear/unblocked, provided that test fluid can flow from the chamber or other supply thereof in the first region through that additional wall and to the first side of the wall portion being tested.

If desired or necessary the enclosure or plenum defining the chamber may be sealable to prevent escape of test fluid therefrom other than through the desired through-holes of the wall portion being tested (or the through-hole(s) of the additional wall, where such is present, as discussed above).

In some embodiments of the invention the flow of the test fluid that is caused or permitted to occur from the first region to the second region may be promoted or facilitated by either natural convective flow of the test fluid from the chamber or other supply to or towards and into the second region, or alternatively or additionally it may be promoted or facilitated by means of a pump which may be provided as an additional component of the apparatus.

In embodiments of the invention the illumination device located in the second region and which illuminates that second region with the appropriate light or other electromagnetic radiation to cause scattering thereof from the active material, may preferably generate a beam, especially a shaped beam, of the radiation in question. That shaped beam may advantageously be a flat or flattened sheet beam of the radiation in question, in order to facilitate the detection of scattered light therefrom.

In many embodiments the beam of the radiation in question may preferably be positioned close to the wall under test and directed across the second region in a transverse manner: that is to say, the beam is directed along an axis which is generally approximately transverse or normal to the direction of any flow of test fluid exiting any substantially unblocked through-holes in the wall portion under test, e.g. generally approximately parallel to a general plane of the wall portion under test.

In embodiments of the invention the detector device which detects the scattering of the light or other electromagnetic radiation incident on the active material in the test fluid exiting the substantially unblocked through-holes in the component wall portion under test, may comprise a camera. Preferably, of course, such a camera is sensitive to the particular electromagnetic radiation emitted by the illumination device. However, other forms or types of detector device may be used, particularly e.g. depending on the precise type of electromagnetic radiation employed.

In practical embodiments the camera or other detector device may be positioned at any suitable location in or adjacent or facing the said second region, in order to provide an optimised physical and/or spatial arrangement for detecting the scattered light or other radiation emanating from through-holes in the component wall portion being tested.

In practical embodiments of the method of the invention, the method may additionally comprise, prior to step (ii) (and optionally prior to or after step (i)), a preliminary step of:
temporarily blocking any through-hole(s) in the wall of the component other than those one or more through-holes in the portion of the component wall which are being tested.

Such a temporary blocking, e.g. by simple application of a removable occluding or fluid-impervious tape or shield element, of the through-hole(s) in any portion of the component wall not being tested, may thus serve to avoid any misreadings or rogue data obtained by inadvertent passage of test fluid through wall(s) or wall portions of the component which are not under test.

In practical embodiments of the method of the invention, the method may additionally comprise, after step (iv) or (v), a step of:
purging the first region, e.g. the interior of the chamber providing the source of the test fluid, of test fluid, in order to vacate the component of test fluid ready for subsequent post-testing use.

Such purging may be accomplished for example by pumping or flowing plain (or substantially pure) air or other purging gas (or even other fluid) through the various through-hole(s) in the one or more component wall(s).

As one or more optional adjunct features or components of the apparatus of the invention, and of the corresponding test method, in some embodiments there may additionally be provided one or more of:
a display device, for displaying in graphical form the results of the detected light (or other radiation) scattering;
a memory device, for storing in electronic form, e.g. in one or more libraries, one or more maps corresponding to said known pattern(s) of through-holes in one or more portions of the wall of the component to be tested, in order to provide a basis for the comparator device to compare the detected scattering with the known through-hole pattern(s);
an analyser device, for analysing, e.g. automatically analysing, the detected scattering pattern(s) and providing corresponding data for processing by the comparator device, which may then compare the data according to one or more predefined algorithms.

Any or all of the above optional adjunct features or components, together with comparator device of the apparatus, may for example be provided by appropriate electronic or computer hardware and/or software in an overall control system for the apparatus and for carrying out at least some of the steps of the test method.

If or as desired or necessary, any suitable form of calibration may be employed prior to carrying out the method, in order to ensure the accuracy and usefulness of the results of the scattering detection and comparison steps.

Within the scope of this application it is expressly envisaged that the various aspects, embodiments, examples and alternatives, and in particular the individual features thereof, set out in the preceding paragraphs, in the claims and/or in the following description and drawings, may be taken independently or in any combination. For example, features defined or described in connection with one embodiment are applicable to any and all embodiments, unless expressly stated otherwise or such features are incompatible.

BRIEF DESCRIPTION OF THE DRAWINGS

Embodiments of the invention will now be described in detail, by way of example only, with reference to the accompanying drawings, in which:

FIG. 1(a) shows the arrangement with the two walls mutually attached and FIG. 1(b) shows the arrangement with two walls detached from one another, and have already been described;

FIG. 2(a) shows a twin-walled unitary integrated component formed e.g. by an ALM technique, and FIG. 2(b) shows an arrangement of a complex, non-straight hole, and have already been described.

DETAILED DESCRIPTION OF EMBODIMENTS OF THE INVENTION

Figure 1:
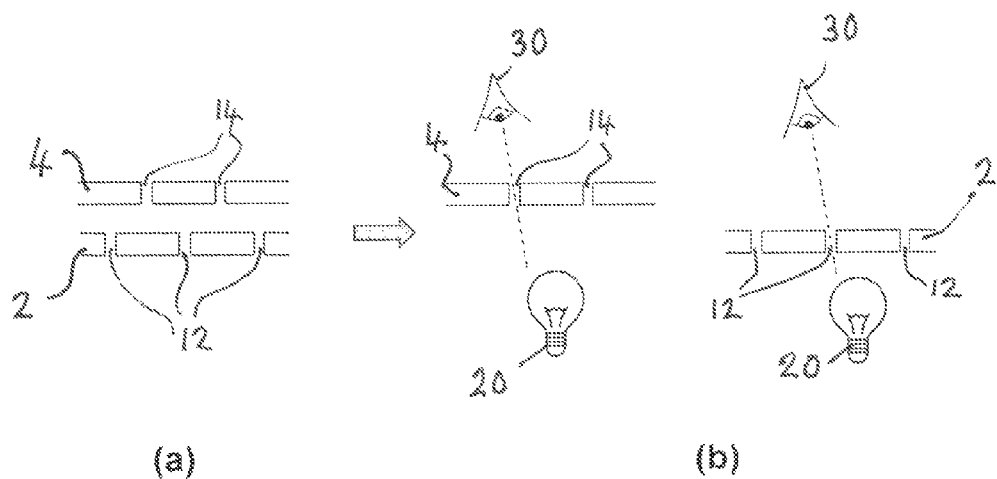
FIG. 1 is an explanatory schematic view of a known simple line-of-sight through-hole inspection technique using visible light, as applied to a separable dual-wall component in which each wall has through-holes therein, where
Figure 2:
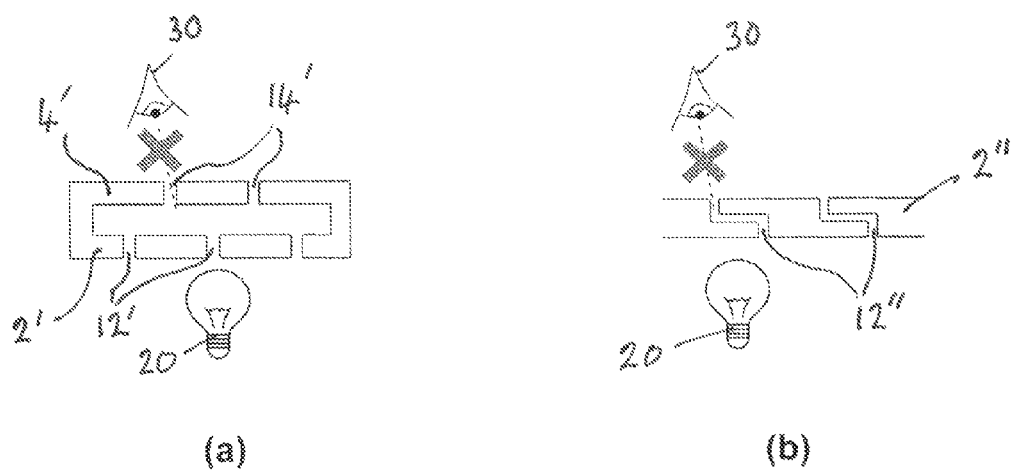
FIG. 2 is an explanatory schematic view, similar to FIG. 1, but showing the corresponding simple line-of-sight through-hole inspection technique using visible light being attempted to be applied—but unsuccessfully—to more complex components, where
Figure 3:
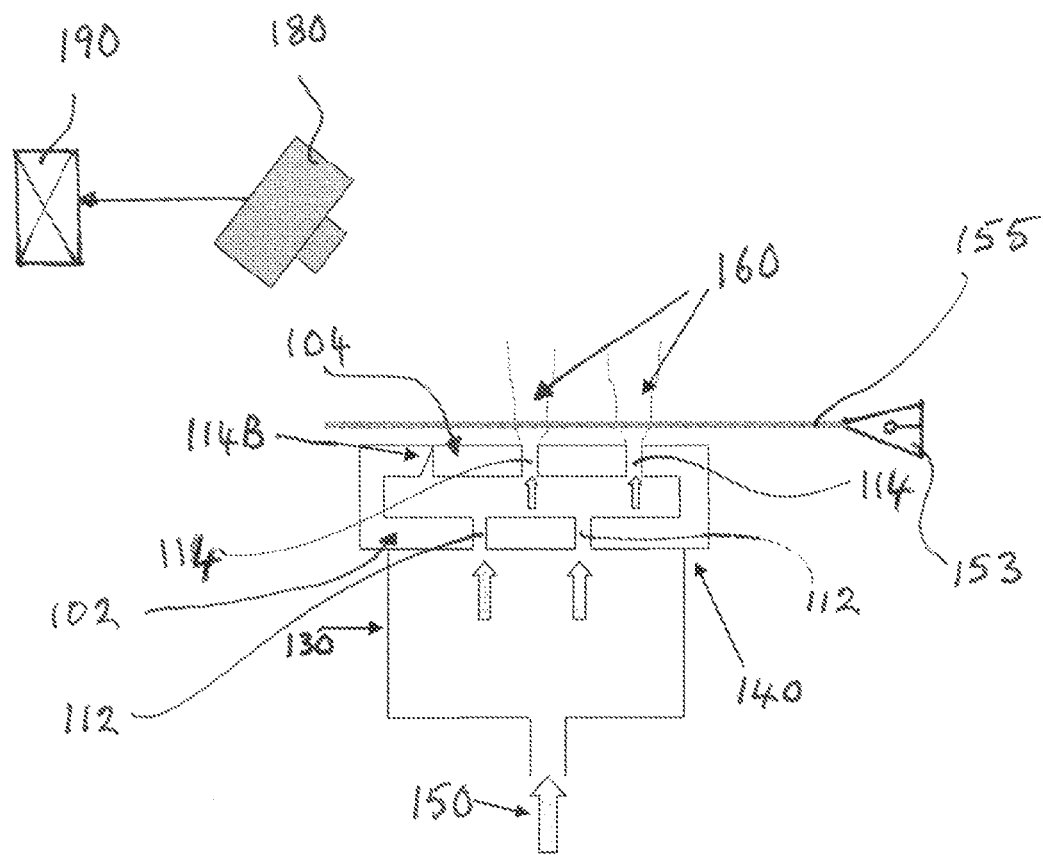
FIG. 3 is schematic view of a test arrangement in accordance with an embodiment of the invention.

Referring to FIG. 3 of the drawings (FIGS. 1 and 2 having already been referred to in the context of the prior art), here there is shown schematically a test arrangement in accordance with an embodiment of the invention. For the most part this illustration will be self-explanatory, in view of the foregoing description and discussion.

As shown in FIG. 3, the engine component comprises a pair of walls 102, 104, which are shown here by way of example as being twin wall sections of a unitarily formed integrated piece, such as that formed by an additive layer deposition (ALM) method. The wall 102 comprises a plurality of through-holes 112 therein, which may be of any number and in any pattern, and the wall 104 likewise comprises a plurality of through-holes 114 therein, again in any number and pattern. In this illustrated example, it is the wall 104 which is to be tested for the occurrence and/or location and/or identity of one or more of the through-holes 114 therein which may be blocked or partially blocked.

The testing apparatus comprises a plenum or chamber 130 which is placed against the wall 102, preferably so as to be sealed thereagainst such as at its edges 140, so as to avoid leakage of test fluid out of the chamber 130 during the test procedure apart from where it is needed and permitted, which is through the through-holes 112 in the wall 102 which lead to the test wall 104. Provided into the chamber 130 is an input supply flow 150 of a test fluid, which may be provided from a separate source thereof (not shown). By way of example the test fluid comprises a colloidal dispersion in air of fine micro-particles of titanium oxide ($TiO_2$), which by its nature is able to readily and significantly scatter visible light incident thereon.

Located to one lateral side of the component 102, 104 is a visible light source 153, e.g. a halogen bulb, LED or other suitable source of visible light, e.g. a laser source, which generates (optionally by use of a focusing or collimating device (not shown)) a flattened sheet-like beam of light 155 which passes transversely across, i.e. normal to, the potential outlet paths 160 of test fluid from each of the through-holes 114 in the component wall 104 under test. Thus, and as shown in the drawing, the sheet beam of light 155 is preferably oriented such that it is positioned close to the test wall 104 and oriented generally substantially parallel to the general plane of the test wall 104, since in this configuration an optimum scattering effect is likely to be achieved. Located above and to an opposite lateral side of the component 102, 104 is a camera 180, linked to an appropriate monitoring, display and control system 190, which comprises appropriate electronic or computer-based hardware and/or software to carry out the various displaying, memory/library functions, analysis and comparator functionalities of the overall test system.

As an alternative to the use of a flattened sheet-like beam of light to illuminate the potential outlet paths 160 of test fluid from each of the through-holes 114 in the component wall 104 under test, if desired or as a possibly more suitable arrangement it may in some cases be possible instead to employ a diffuse light source in combination with an appropriate active scattering material-containing test fluid, e.g. smoke, which is able to exhibit particularly well-defined or pronounced differences in flow concentration, in marked contrast to the surrounding medium, as the relevant outlet flow(s) 160 of test fluid emerge from the relevant hole(s) 114 under test. In this manner such particularly pronounced or sudden changes in flow concentration can then be readily observed and/or detected in a relatively upstream region of the respective outlet flow, even with a relatively diffuse light beam, before such a flow loses its high-definition and its detected scattering signal may be lost or become weak further downstream in the respective outlet flow.

Preliminarily, in order to focus the test procedure on the portion of the wall 104 which is actually to be tested for hole blockages, any other through-holes in the wall 104 which are not being tested should preferably be blocked temporarily, e.g. by application of a fluid-impervious or occluding tape or shield element to that non-test portion of the wall 104.

In the implementation of the test method of the invention embodiment, as the input supply flow of test fluid 150 passes through the through-holes 112 in the non-test wall 102 (which holes 112 may or may not be blocked, since this does not matter as this wall 102 is not under test), it enters the chamber 130. From there, by natural convection (or alternatively under the action of a pump (not shown)) the test fluid flow enters and passes through those one or more of the through-holes 114 in the test wall 104 which are substantially clear and unblocked and so permit the passage of the test fluid therethrough to form output flows 160. Two only of those holes 114 are shown as clear and unblocked in the illustrated example.

However, as shown in the drawing, one of those holes—labelled 114B—is substantially blocked, e.g. from accumulated debris or deposits arising from use of the engine, which causes there to be substantially no flow of the test fluid through and out of that hole 114B. Given that the overall pattern of through-holes 114 in the component wall 104 under test is known, by comparing (such as by using a suitable predefined algorithm) the detected light scattering pattern arising from the output flows 160 from the clear/unblocked holes 114 with that known overall hole pattern in the wall 104, the occurrence, location and identity of the blocked hole 114B can be readily determined, and therefore remedial action taken to clear it.

In the event that the hole 114B were to be only partially blocked, this would probably lead instead to a reduced flow, possibly a significantly reduced flow, of the test fluid through that hole 114, leading to a significantly reduced level of light scattering in the fluid flow exiting that hole 114. This would still be readily detectable by the camera and associated comparator/analysis system 180, 190, and so could just as readily be determined as for a completely blocked hole.

Although one embodiment of the invention has been described and illustrated here with reference to an integrated multi-walled or non-line-of-sight design of component, it is to be understood that embodiments of the invention may be applied to any type of component with at least one wall therein containing one or more through-holes which need to be periodically tested for possible blockages.

Subsequent to the test procedure, remnant test fluid remaining within the component 102, 104, and in particular that still present in any of the through-holes 112, 114, can be readily removed by purging the arrangement with a purging gas, e.g. clean air. In the case of dispersed particles of an oil or other liquid (e.g. dry-ice condensed water vapour) being used as the active scattering material, a purging flow of heated air may be used instead in order to burn off and exhaust the oil or aqueous material. A final drying stage may optionally be carried if desired or necessary, such as by use of a final flow of heated air.

In order to test for blockages in through-holes 112 in the initial non-test wall 102 of the component, the component can simply be reversed and the procedure repeated, in which case the flow of test fluid passes through the various through-holes in the opposite directions.

Embodiments of the invention may be applied to the inspection or testing for flow blockages in through-holes of any engine component where e.g. a large number of holes are present, such as turbine blades, guide vanes, effusion cooled exhaust ducts, combustor tiles, combustor heat shields, or combustor cassettes. Embodiments of the invention may be especially useful for the inspection or testing of integrated components such as those manufactured using ALM (or direct laser deposition (DLD)) methods. By use of the invention, quicker and more efficient testing of such engine parts may be achieved, resulting in time and cost savings in e.g. servicing and maintenance regimes.

Instead of using an at least partially automated test procedure, a somewhat simplified version of the above-described method may be to use a manual inspection process to visualise the light-scattering flow emanating from each respective through-hole. To make this easier, controlled selective lighting, or diffuse lighting, could be used to make the task of identifying scattered light flows easier.

In other variants, selected portions of the component wall under test may be constituted by particular selected rows of through-holes, so that individual rows may be tested separately and possibly sequentially. Also, coloured active light-scattering material may be used to provide a higher degree of contrast in the scattering detection step, thereby making blockage identification even more efficient and robust.

It is to be understood that the above description of embodiments and aspects of the invention has been by way of non-limiting examples only, and various modifications may be made from what has been specifically described and illustrated whilst remaining within the scope of the invention as defined in the appended claims.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Furthermore, features, integers, components, elements, characteristics or properties described in conjunction with a particular aspect, embodiment or example of the invention are to be understood to be applicable to any other aspect, embodiment or example described herein, unless incompatible therewith.

The invention claimed is:

1. A method for testing an engine component for blockage of one or more through-holes in at least a portion of a wall thereof, wherein the portion of the wall comprises a known pattern of through-holes therein extending between first and second sides of the wall, the method comprising:
   (i) providing in a first region to the first side of the wall a supply of a test fluid, wherein the test fluid comprises a material able to scatter electromagnetic radiation incident thereon;
   (ii) causing or permitting a flow of the test fluid to occur from the first region to a second region to the second side of the wall;
   (iii) illuminating the second region with electromagnetic radiation to cause scattering of electromagnetic radiation by material exiting substantially non-blocked through-holes in the wall portion having passed therethrough from the first side to the second side;
   (iv) detecting said scattering of electromagnetic radiation from said substantially non-blocked through-holes; and
   (v) comparing said detected scattering of electromagnetic radiation from said substantially non-blocked holes with the known pattern of through-holes in the component wall portion to determine the presence and/or location and/or identity of any blocked or partially blocked through-holes in the component wall portion.

2. The method according to claim 1, wherein the electromagnetic radiation is visible light.

3. The method according to claim 1, wherein the active scattering material is provided in the form of particles of a solid material or as particles or droplets of a liquid material.

4. The method according to claim 3, wherein the particles of the active scattering material are provided as dispersed particles or micro-particles in a gaseous carrier medium.

5. The method according to claim 1, wherein the active scattering material is selected from one or more of:
   solid micro-particles of titanium dioxide ($TiO_2$),
   flakes of aluminium (Al) metal,
   smoke,
   a gaseous dispersion of a radiation-scattering oil,
   water vapour,
   micro-particles or micro-spheres of glass or a glass material,
   particles of a coloured light-scattering material or a fluorescent material.

6. The method according to claim 1, wherein the supply of the fluid is in the form of a reservoir of the test fluid, wherein optionally the reservoir comprises an enclosure or plenum which defines a chamber within which a volume of the test fluid may be stored or provided for supply to the component being tested.

7. The method according to claim 6, wherein:
   (i) the reservoir is configured to be placeable against a sidewall of the component whose wall portion with through-holes therein is to be tested, and that sidewall against which the reservoir is placeable is the said component wall portion with through-holes which is to be tested; or
   (ii) the reservoir is configured to be placeable against a sidewall of the component whose wall portion with through-holes therein is to be tested, and that sidewall against which the reservoir is placeable is an additional wall of the component, also with one or more through-holes therein, which is spaced from and/or joined to the said component wall portion to be tested.

8. The method according to claim 6, wherein the reservoir comprises the said enclosure or plenum, and the said enclosure or plenum is sealable to prevent escape of test fluid therefrom other than through the through-holes of the component wall portion under test.

9. The method according to claim 1, wherein the flow of the test fluid that is caused or permitted to occur from the first region to the second region is promoted or facilitated by either:

(i) natural convective flow of the test fluid from the chamber or other supply to or towards and into the second region, or alternatively or additionally (ii) by means of a pump.

10. The method according to claim 1, wherein the illumination device located in the second region and which illuminates that second region with the electromagnetic radiation to cause scattering thereof from the active material generates a shaped beam of the radiation in question, optionally a flat or flattened sheet beam of the radiation.

11. The method according to claim 10, wherein the beam of the radiation is directed across the second region along an axis which is generally transverse or normal to the direction of any flow of test fluid exiting any substantially unblocked through-holes in the wall portion under test, optionally generally parallel to a general plane of the wall portion under test.

12. The method according to claim 1, wherein the detector device which detects the scattering of the electromagnetic radiation incident on the active material in the test fluid exiting the substantially unblocked through-holes in the component wall portion under test comprises a camera.

13. The method according to claim 1, additionally comprising:

prior to step (ii) (and optionally prior to or after step (i)), a preliminary step of temporarily blocking any through-hole(s) in the wall of the component other than those one or more through-holes in the portion of the component wall portion which are being tested; and/or after step (iv) or step (v), a step of purging the first region of test fluid, in order to vacate the component of test fluid ready for subsequent post-testing use.

14. An apparatus for testing an engine component for blockage of one or more through-holes in at least a portion of a wall thereof, wherein the portion of the wall comprises a known pattern of through-holes therein extending between first and second sides of the wall, the apparatus comprising:

a supply of a test fluid located in a first region to the first side of the wall, wherein the test fluid comprises a material able to scatter electromagnetic radiation incident thereon, an illumination device located in a second region to the second side of the wall for illuminating said second region with electromagnetic radiation to cause scattering of electromagnetic radiation by material exiting substantially non-blocked through-holes in the wall portion having passed therethrough from the first side to the second side of the wall under a flow of the test fluid caused or permitted to occur from the first side to the second side, a detector device for detecting said scattering of electromagnetic radiation from said substantially non-blocked through-holes, and a comparator device for comparing said detected scattering of electromagnetic radiation from said substantially non-blocked holes with the known pattern of through holes in the component wall portion to determine the presence and/or location and/or identity of any blocked or partially blocked through holes in the component wall portion.

15. The apparatus according to claim 14, further comprising one or more of:

a display device, for displaying in graphical form the results of the detected radiation scattering;

a memory device, for storing in electronic form one or more maps corresponding to said known pattern(s) of through-holes in one or more portions of the wall of the component to be tested, for providing a basis for the comparator device to compare the detected scattering with the known through-hole pattern(s);

an analyser device, for analysing the detected scattering pattern(s) and providing corresponding data for processing by the comparator device.

* * * * *